United States Patent [19]

Morita et al.

[11] Patent Number: 5,292,926
[45] Date of Patent: Mar. 8, 1994

[54] CYSTEINE DERIVATIVES

[75] Inventors: Takakazu Morita, Toyonaka; Tadashi Iso, Kawachinagano; Shiro Mita, Ashiya; Yoichi Kawashima, Kyoto, all of Japan

[73] Assignee: Santen Pharmaceutical Co., Ltd., Osaka, Japan

[21] Appl. No.: 44,908

[22] Filed: Apr. 8, 1993

Related U.S. Application Data

[63] Continuation of Ser. No. 610,346, Nov. 5, 1990, abandoned, which is a continuation of Ser. No. 298,189, Jan. 17, 1989, abandoned.

Foreign Application Priority Data

Jan. 25, 1988 [JP] Japan .................. 63-14189

[51] Int. Cl.$^5$ .......................................... C07C 321/00
[52] U.S. Cl. ............................... 560/147; 560/16; 560/153; 562/431; 562/426; 562/556; 562/557; 564/198
[58] Field of Search .................. 560/147; 562/557; 564/154

[56] References Cited

U.S. PATENT DOCUMENTS

| | | | |
|---|---|---|---|
| 4,053,651 | 10/1977 | Ondetti | 562/556 |
| 4,137,420 | 1/1979 | Fujita | 562/557 |
| 4,241,086 | 12/1980 | Iwao | 514/562 |
| 4,305,958 | 12/1981 | Fujita | 562/557 |
| 4,401,677 | 8/1983 | Greenberg | 514/562 |
| 4,507,316 | 3/1985 | Youssefyeh | 514/562 |

*Primary Examiner*—Michael L. Shippen
*Attorney, Agent, or Firm*—Frishauf, Holtz, Goodman & Woodward

[57] ABSTRACT

This invention relates to cysteine derivatives of the formula[I] and salts thereof.

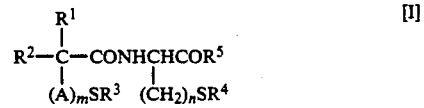

The compounds of this invention are useful for immunomodulator and treatment of liver disorder.

5 Claims, No Drawings

CYSTEINE DERIVATIVES

This application is a continuation of application Ser. No. 07/610,346, filed Nov. 5, 1990, now abandoned which is a continuation of application Ser. No. 07/298,189 filed Jan. 17, 1989 (abandoned).

DETAILED DESCRIPTION OF THE INVENTION

This invention relates to cysteine derivatives of the formula[I] and salts thereof,

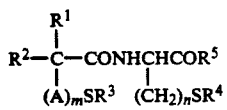

wherein
- $R^1$ is lower alkyl;
- $R^2$ is lower alkyl;
- $R^3$ and $R^4$ are the same or different hydrogen, lower alkyl, lower alkanoyl, (substituted)phenyl lower alkyl, (substituted)phenylcarbonyl, furoyl or thenoyl;
- $R^5$ is hydroxy, lower alkoxy, amino or lower alkylamino;
- A is straight or branched lower alkylene;
- m is 0 or 1;
- n is 1 or 2 with the proviso that
when m is 0, n is 1 and $R^5$ is hydroxy, at least either the $R^3$ or $R^4$ is (substituted)phenyl lower alkyl, (substituted)-phenylcarbonyl, furoyl or thenoyl; and
when n is 2, $R^4$ should not be lower alkyl.

The same shall be applied hereinafter.

The terms defined above are explained as follows in more detail.

The term "lower alkyl" intends to designate straight or branched $C_1$-$C_6$ lower alkyl exemplified by methyl, ethyl, propyl, isopropyl and hexyl.

The term "lower alkanoyl" intends to designate straight or branched $C_1$-$C_6$ lower alkanoyl exemplified by acetyl, propionyl, pivaloyl and hexanoyl.

The word "(substituted)" in (substituted)phenyl lower alkyl and (substituted)phenylcarbonyl intends to designate that phenyl nucleus thereof can be substituted by lower alkyl, lower alkoxy or halogen.

There are various studies on cysteine derivatives and such studies were reported in U.S. Pat. Nos. 4305958, 4241086, 4255446 etc.

The cysteine derivatives are known to have many kinds of efficacy such as suppression of liver disorders and anti-rheumatism. But, there are very few studies which reported the influence on pharmacological efficacy by incorporation of alkylene group in the side chain of cysteine derivatives, expansion of the alkylene length of the side chain or by substitution of radicals. So, we studied cysteine derivatives in more detail.

We synthesized various novel cysteine derivatives and examined their pharmacological effects, especially effect of incorporation of alkylene group in the side chain of the cysteine derivatives and expansion of the alkylene length of the side chain.

From the results of the pharmacological examination, which are described later in the article of pharmacological test, we found that the compounds of this invention have excellent supressing effect on liver disorders and immunomodulating effect.

The compounds of the formula[I] can be prepared by the similar methods shown in U.S. Pat. Nos. 4305958 and 4255446 or Japanese Patents Publication 12119/1984.

The typical methods are shown below.

(A) The compound of the formula[I] can be prepared by the reaction of amino acid derivative of the formula[II] with carboxylic acid derivative of the formula[III] or active derivative thereof.

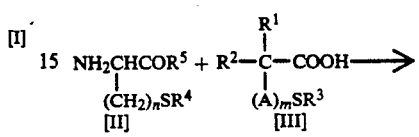

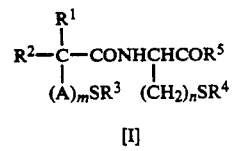

Active derivative defined above is reactive derivative of carboxylic acid exemplified by acid chloride, acid anhydride and mixed acid anhydride. Active derivative of the compound of the formula[III] can be converted into the compound of the formula[I] by the usual method such as Schotten-Baumann method which is generally used for condensation of amine derivative with carboxylic acid derivative.

Carboxylic acid of the formula [III] can be converted directly into the compound of the formula[I] using a condensing agent such as N,N'-dicyclohexylcarbodiimide(DCC).

It is not necessary to specify a reaction condition such as temperature or reaction time.

(B) The compound of the formula[I] can be prepared by the reaction of amino acid derivative of the formula[II] with polythioester of the formula[IV],

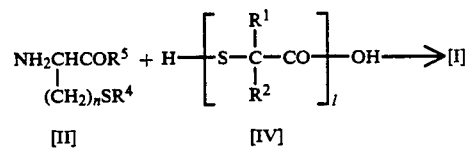

wherein l is a polymerization degree having a mean molecule weight of about 200–1500.

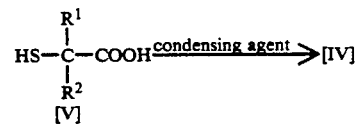

The compound of the formula[IV] can be prepared from the corresponding monomer of the formula[V] using a condensing agent such as DCC in an organic solvent.

It is not necessary to specify conditions of condensation of the compound of the formula[II] with the compound of the formula [IV],but, the reaction is usually performed in a presence of base such as sodium carbonate or potassium carbonate.

In connection with the above methods (A) and (B):
1) When $R^3$ and/or $R^4$ are/is hydrogen, if necessary, the group(s) can be converted into other groups than hydrogen after the above-mentioned reaction. The conversion can be performed using a known method which is used for an introduction of a protective group etc. to a thiol group.
2) When $R^5$ is hydroxy, if necessary, the group can be converted into ester or amide after the above-mentioned reaction. The conversion can be performed using a known method which is used for conversion of a carboxylic group to ester or amide.
3) When the group defined in $R^3$, $R^4$ or $R^5$ is used as protective group, if necessary, such group can be removed after the above-mentioned reaction. The removal can be performed by a known method.

The compound of the formula[I] can be converted into pharmaceutically acceptable salts of inorganic or organic base.

Examples of the salts are sodium salt, potassium salt, diethylamine salt and triethanolamine salt.

The compounds of this invention have stereoisomers because of the existence of one or more asymmetric carbon atom, and these isomers are included in this invention.

A liver disorder model caused by an administration of $CCl_4$ to a rat is widely used to examine efficacy of a compound on liver diseases.

GOT and GPT values in the serum are used as an indication of a degree of liver disorder. If the value, which is raised by liver disorder, falls by an administration of a compound, the compound is judged effective on liver dosorder.

As the result of the experiment, whose detailed data are shown in the article of pharmacological test, using the compounds of this invention, we found that the activity of serum transaminase in the group treated with the compound of this invention is significantly decreased as compared with that in the untreated group. The experiment prove that the compound of this invention have a suppressive effect on liver disorder.

Recently, immunity has been thought to closely relate to the mechanism of development and chronicity of liver disorder. To examine influence of the compound of this invention on immune system, we examined the immune response against sheep red blood cells in mice, which is usually used to examine immunomodulating effect.

This experimental method is to examine the efficacy on the immune system according to increase or decrease of the number of haemolytic plague-forming cells of mouse spleen cells. As shown in the pharmacological test, the compound of this invention shows an excellent immunosuppressive effect.

A compound, which has a similar chemical structure to the compounds of this invention, is disclosed in U.S. Pat. No. 4305958. It is generally recognized that very slight modification of the chemical structure greatly influences the efficacy of a compound. So, we examined how the modification of the chemical structure influences to the efficacy.

We made the comparative test on the immunosuppressive effect of the compound of this invention and known compound represented by the formula[VI].

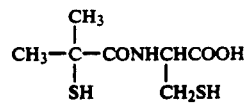

As shown in the pharmacological test, the compound of this invention shows more effect than the compound described in the U.S. Patent.

As the result, we found that the compound of this invention must be a new type of drug for liver diseases because the compound decreased the value of GOT and GPT in serum and suppressed the immunity.

Furthermore, the compound of this invention can be used as a drug for autoimmune diseases such as rheumatoid arthritis.

The compound(s) of this invention can be administered either orally or parenterally. Examples of dosage forms are tablet, capsule, powder, granule, suppository, injection, eye drops and percutaneous.

The dosage is adjusted depending on symptom, dosage form, etc., but usual daily dosage is 1 to 5000 mg in one or a few divided doses.

Examples of preparations of the compounds and formulations are shown below.

EXAMPLE

EXAMPLE 1

N-(2-Mercapto-2-Methylpropionyl)-DL-Homocysteine (Compound No. 1)

To a stirred solution of 2-mercapto-2-methylpropionic acid (40.4 g) in ethyl acetate(200 ml), N,N'-dicyclohexylcarbodiimide (69.3 g) dissolved in ethyl acetate(200 ml) was added dropwise under ice-cooling. After the addition, the reaction mixture was stirred for 1 hour at room temperature and filtered. The filtrate was concentrated in vacuo. To the residue, 400 ml of N,N-dimethylformamide(DMF) was added to give DMF solution of polythioester.

To a mixture of DL-homocysteine(37.9 g), potassium carbonate(77.4 g), water(400 ml) and DMF(100 ml), the polythioester solution was added and the reaction mixture was stirred overnight at room temperature. Water(21) was added to the reaction mixture and washed with ethyl acetate. The aqueous layer was acidified with 6N hydrochloric acid and extracted with ethyl acetate. The organic layer was washed with saturated sodium chloride solution, dried over anhydrous sodium sulfate and concentrated in vacuo. The oily residue was purified by a silica gel column chromatography and recrystallized with isopropyl ether to give 39.8 g(59.9%) of the titled compound.

mp 102°-104° C. (isopropyl ether)

IR(KBr, cm$^{-1}$) 3405, 3335, 2536, 1714, 1599, 1524, 1412, 1296, 1270, 1254, 1213, 1186, 658

EXAMPLE 2

N-(2,2-Dimethyl-3-Mercaptopropionyl)-L-Cysteine (Compound No. 2)

DMF solution of polythioester was prepared using 3-mercaptopivalic acid(40.3 g) and N,N'-dicyclohexylcarbodiimide (61.9 g) by the similar method as Example 1.

The polythioester solution was added to a mixture of L-cysteine hydrochloride monohydrate(52.7 g), potassium carbonate (124 g), water(400 ml) and DMF(100 ml). The mixture was stirred overnight at room temperature and followed by the similar method as Example 1 to give 47.2 g(66.3%) of the titled compound.

mp 83.5°-85.5° C. (isopropyl ether)

IR (KBr, cm$^{-1}$) 3352, 2596, 1728, 1630, 1528, 1424, 1403, 1296, 1204, 870, 593

Optical Rotation $[\alpha]_D^{25} - 3.3°$ (c=1.0, methanol) and $[\alpha]_D^{25} + 57.8°$ (c=1.0, chloroform)

The following compound was prepared by the similar method as Example 2.

N-[(2-Ethyl-2-Mercaptomethyl)Butyryl]-L-Cysteine (Compound No. 3)

IR (KBr, cm$^{-1}$) 3350, 1726, 1628, 1526

EXAMPLE 3

S-Benzyl-N-(3-Benzylthio-2,2-Dimethylpropionyl)-L-Cysteine (Compound No. 4)

To a stirred solution of S-benzyl-L-cysteine(11.5 g) in 2N sodium hydroxide solution(68 ml), 3-benzylthio-2,2-dimethylpropionyl chloride (14.6 g) dissolved in ether(10 ml) was added dropwise under ice-cooling. After the addition, the reaction mixture was stirred for 20 minutes under ice-cooling and 2 hours at room temperature. The reaction mixture was acidified with 6N hydrochloric acid and extracted with ethyl acetate. The organic layer was washed with saturated sodium chloride solution, dried over anhydrous sodium sulfate and concentrated in vacuo. The oily residue was purified by a silica gel column chromatography to give 19.4 g(85.1%) of the titled compound.

IR(film, cm$^{-1}$) 3344, 1731, 1620, 1514, 1495, 1236, 1199, 700

Optical Rotation $[\alpha]_D^{25} - 31.5°$ (c=1.1, methanol)

The following compound was prepared by the similar method as Example 3.

S-Benzyl-N-(3-Benzylthio-2,2-Dimethylpropionyl)-D-Cysteine (Compound No. 5)

IR(film, cm$^{-1}$) 3344, 1729, 1620, 1513, 1495, 1236, 1200, 699

Optical Rotation $[\alpha]_D^{25} + 33.0°$ (c=1.0, methanol)

EXAMPLE 4

N-(2,2-Dimethyl-3-Mercaptopropionyl)-L-Cysteine (Compound No. 2)

To a solution of S-benzyl-N-(3-benzylthio-2,2-dimethylpropionyl)-L-cysteine (18.0 g) in liquid ammonia(250 ml), metallic sodium (5.0 g) cut into small pieces was added. To this solution, ammonium chloride was added and then liquid ammonia was evaporated. To the residue, water was added, and the solution was washed with ethyl acetate. The aqueous layer was acidified with 6N hydrochloric acid and extracted with ethyl acetate. The organic layer was washed with saturated sodium chloride solution, dried over anhydrous sodium sulfate and concentrated in vacuo. The oily residue was purified by a silica gel column chromatography and recrystallized with a mixture of ethyl acetate and cyclohexane to give 7.1 g(69.6%) of the titled compound. The physical data were identical with those of the compound obtained in Example 2.

The following compound was prepared by the similar method as Example 4.

N-(2,2-Dimethyl-3-Mercaptopropionyl)-D-Cysteine (Compound No. 6)

mp 83.5°-85.0° C. (ethyl acetate - cyclohexane)

IR(KBr, cm$^{-1}$) 3352, 2595, 1725, 1624, 1522, 1421, 1401, 1295, 1201, 867, 590.

Optical Rotation $[\alpha]_D^{25} - 57.1°$ (c=1.0, chloroform).

EXAMPLE 5

N-[2,2-Dimethyl-3-(Methylthio)propionyl]-S-Methyl-L-Cysteine Dicyclohexylamine Salt (Compound No. 7)

N-(2,2-Dimethyl-3-mercaptopropionyl)-L-cysteine(23.7 g) was dissolved in a solution of potassium carbonate(41.5 g) in water (150 ml) under ice-cooling. To this solution, methyl iodide (36.9 g)was added. After the addition, the reaction mixture was stirred for 30 minutes under ice-cooling and for 1 hour at room temperature. To the reaction mixture, 1N iodine solution(15 ml) was added and the solution was washed with ethyl acetate. The aqueous layer was acidified with 6N hydrochloric acid and extracted with ethyl acetate. The organic layer was washed with sodium hydrogen sulfide solution and saturated sodium chloride solution, dried over anhydrous sodium sulfate and concentrated in vacuo. The oily residue was purified by a silica gel column chromatography. Dicyclohexylamine was added to the oily product to give crystals. The crystals were recrystallized with a mixture of ethyl acetate and hexane to give 29.0 g(65.0%) of the titled comopound.

mp 98°-99.0° (ethyl acetate - hexane)

IR(KBr, cm$^{-1}$) 3380, 2912, 2848, 1635, 1561, 1498, 1409, 1392, 587

Optical Rotation $[\alpha]_D^{25} + 18.6°$ (c=1.0, methanol)

EXAMPLE 6

N-[2,2-Dimethyl-3-(Methylthio)Propionyl]-L-Cysteine Dicyclohexylamine Salt (Compound No. 8)

L-Cysteine hydrochloride monohydrate (15.6 g) was dissolved in a solution of potassium carbonate(46.8 g) in water(150 ml). To this solution, 2,2-dimethyl-3-(methylthio)propionyl chloride (15.6 g) was added dropwise. After the addition, the reaction mixture was stirred for 1 hour at room temperature and washed with ethyl acetate. The aqueous layer was acidified with 6N hydrochloric acid and extracted with ethyl acetate. The organic layer was washed with saturated sodium chloride solution, dried over anhydrous sodium sulfate and concentrated in vacuo. The oily residue was purified by a silica gel column chromatography. Dicyclohexylamine was added to the oily product to give crystals. The crystals were recrystallized with a mixture of ethyl acetate and hexane to give 28.5 g(70.1%) of the titled compound.

mp 122.0°-123.5(ethyl acetate - hexane)

IR(KBr, cm$^{-1}$) 3404, 2920, 2852, 1629, 1560, 1483, 1412, 1383

Optical Rotation $[\alpha]_D^{25} + 35.0°$ (c=1.1, methanol)

EXAMPLE 7

N-(2,2-Dimethyl-3-(Benzoylthio)Propionyl)-S-Methyl-L-Cysteine (Compound No. 9)

To a stirred mixture of S-methyl-L-cysteine(6.5) dissolved in 1.6M aqueous potassium carbonate solution(50 ml) and acetone (50 ml), 2,2-dimethyl-3-(benzoylthio)-propionyl chloride (bp 138°-145°/1.0 mmHg, 12.3 g) was added dropwise under ice-cooling. After 10 minutes, the reaction mixture was stirred for 2 hours at room temperature. The reaction mixture was acidified with 2N hydrochloric acid and extracted with ethyl acetate. The organic layer was washed with water, dried over anhydrous magnesium sulfate and concentrated in vacuo. The oily residue was purified by a silica gel column chromatography to give 12.4 g(72%) of the titled compound.

As dicyclohexylamine salt:
mp 101°-102° C. (ethyl acetate - hexane)
IR(KBr, cm$^{-1}$) 3372, 2912, 2852, 1632
Optical Rotation $[\alpha]_D^{25}$ +11.8° (c=1.0, methanol)

EXAMPLE 8

N-(2,2-Dimethyl-3-Mercaptopropionyl)-S-Methyl-L-Cysteine (Compound No. 10)

To a stirred solution of N-[2,2-dimethyl-3-(benzoylthio)propionyl]-S-methyl-L-cysteine (10.0 g) in methanol(20 ml), 28% ammonia water(40 ml) was added and the mixture was stirred for 2 hours at room temperature. The reaction mixture was washed with ethyl acetate, acidified with 6N hydrochloric acid and extracted with ethyl acetate.

The organic layer was washed with saturated sodium chloride solution, dried over anhydrous magnesium sulfate and concentrated in vacuo. The oily residue was purified by a silica gel column chromatography to give 5.8 g(82%) of the titled compound. As dicyclohexylamine salt:
mp 97°-99° C. (ethyl acetate - hexane)
IR(KBr, cm$^{-1}$) 3364, 2916, 2852, 1635, 1559
Optical Rotation $[\alpha]_D^{25}$ +9.5° (c=1.05, methanol)

EXAMPLE 9

N-(2-Mercapto-2-Methylpropionyl)-S-Trityl-L-Cysteine (Compound No. 11)

To a stirred solution of N-(2-mercapto-2-methylpropionyl)-L-cysteine (11.2 g) in dimethylformamide(50 ml), trityl chloride(16.7 g) was added slowly. The reaction mixture was stirred for 2 hours at room temperature, poured into water and extracted with ethyl acetate. The organic layer was washed with water and saturated sodium chloride solution, dried over anhydrous magnesium sulfate and concentrated in vacuo. The oily residue was purified by a silica gel column chromatography to give 14.2 g(60%) of the titled compound.

IR(film, cm$^{-1}$) 3356, 2976, 1735.
Optical Rotation $[\alpha]_D^{25}$ +19.1° (c=1.52, methanol).

EXAMPLE 10

S-p-Methoxybenzyl-N-(2-p-Methoxybenzylthio-2-Methylpropionyl)-L-Cysteine (Compound No. 12)

To a stirred solution of N-(2-mercapto-2-methylpropionyl)-L-cysteine (2.0 g) in ethanol(10 ml), 4N sodium hydroxide solution(7.7 ml) and paramethoxybenzyl chloride(3.0 ml) were added dropwise under ice-cooling and under nitrogen atomosphere. After the addition, the reaction mixture was stirred for 2 hours under ice-cooling and 2 hours at room temperature. The reaction mixture was concentrated in vacuo, acidified with 2N hydrochloric acid and extracted with ether. The organic layer was washed with saturated sodium chloride solution, dried over anhydrous sodium sulfate and concentrated in vacuo to give crystals. The crystals were recrystallized with ether to give 2.8 g(67%) of the titled compound.

mp 112°-113° C. (ether)
IR(KBr, cm$^{-1}$) 2948, 2924, 1748, 1622, 1609, 1507, 1230, 1165, 1028, 833
Optical Rotation $[\alpha]_D^{25}$ −22.8° (c=0.95, methanol)

EXAMPLE 11

S-p-Methoxybenzyl-N-(2-p-Methoxybenzylthio-2-Methylpropionyl)-L-Cysteine Methyl Ester (Compound No. 13)

To a stirred solution of S-p-methoxybenzyl-N-(2-p-methoxybenzylthio-2-methylpropionyl)-L-cysteine (3.0 g) in dimethylformamide(20 ml), sodium hydride(0.3 g) was added under nitrogen atomosphere at room temperature and the mixture was stirred for 1 hour. Methyl iodide(0.5 ml) was added to the mixture. The reaction mixture was stirred for 4 hours at room temperature. Water(300 ml) was added to the reaction mixture and extracted with ether. The organic layer was washed with saturated sodium chloride solution, dried over anhydrous sodium sulfate and concentrated in vacuo. The oily residue was purified by a silica gel column chromatography to give 2.8 g(90%) of the titled compound.

IR(film, cm$^{-1}$) 1742, 1665, 1610, 1512, 1301, 1244, 1175, 1031, 832.
Optical Rotation $[\alpha]_D^{25}$ −31.9° (c=0.77, methanol).

EXAMPLE 12

S-p-Methoxybenzyl-N-(2-p-Methoxybenzylthio-2-Methylpropionyl)-L-Cysteine Amide (Compound No. 14)

S-p-Methoxybenzyl-N-(2-p-methoxybenzylthio-2-methylpropionyl)-L-cysteine methyl ester(2.4 g) was dissolved in methanol(50 ml) saturated with ammonia gas. To this solution, ammonia gas was bubbled for 20 minutes. The reaction mixture was stored for 2 days at room temperature and concentrated in vacuo to give crystals. The crystals were recrystallized with methanol to give 1.5 g(65%) of the titled compound.

mp 116°-117° C. (methanol)
IR(KBr, cm$^{-1}$) 1691, 1621, 1617, 1607, 1502, 1402, 1232, 1174, 1029
Optical Rotation $[\alpha]_D^{25}$ −1.6° (c=0.74, methanol)

EXAMPLE 13

N-(2-Mercapto-2-Methylpropionyl)-L-Cysteine Amide (Compound No. 15)

To a solution of S-p-methoxybenzyl-N-(2-p-methoxybenzylthio-2-methylpropionyl)-L-cysteine amide(500 mg) in liquid ammonia(10 ml), metallic sodium(0.15 g) was added under nitrogen atomosphere at −78° C. Ammonium chloride was added to the solution and ammonia was evaporated. Methanol and methylene chloride were added to the residue and filtered. The filtrate was concentrated in vacuo and the oily residue was purified by a silica gel column chromatography to give 80 mg(32%) of the titled compound.

mp 124°-125° C. (ethyl acetate - hexane)
IR(KBr, cm$^{-1}$) 2540, 1659, 1653, 1633, 1530, 1126, 634
Optical Rotation $[\alpha]_D^{25}$ +0.3° (c=0.60, methanol)

EXAMPLE 14

N-(2-Mercapto-2-Methylpropionyl)-L-Cysteine Methyl Ester (Compound No. 16)

To a solution of N-(2-mercapto-2-methylpropionyl)-L-cysteine (1.0 g) in ether(3 ml), diazomethane dissolved in ether(12 ml) was added dropwise under ice-cooling. After the addition, acetic acid was added to the reaction mixture. The reaction mixture was washed with saturated sodium hydrogen carbonate solution and saturated sodium chloride solution, dried over anhydrous sodium sulfate and concentrated in vacuo. The oily residue was purified by a silica gel column chromatography to give 1.0 g(94%) of the titled compound.

IR(film, cm$^{-1}$) 2540, 1739, 1656, 1502, 1437, 1347, 1212, 1177

Optical Rotation $[\alpha]_D^{25} - 18.2°$ (c=0.88, methanol)

EXAMPLE 15

N-(2-Mercapto-2-Methylpropionyl)-L-Cysteine N,N-Dimethylamide (Compound No. 17)

To a stirred solution of N-(2-mercapto-2-methylpropionyl)-L-cysteine (1.0 g) in methylene chloride(4 ml), dicyclohexylcarbodiimide (0.5 g) dissolved in methylene chloride(4 ml) was added dropwise. After the addition, the reaction mixture was stirred for 30 minutes under ice cooling and for 1 hour at room temperature. Dimethylamine hydrochloride(0.2 g) and triethylamine(0.4 ml) dissolved in a mixture of methylene chloride (2 ml) and methanol(1 ml) was added dropwise under ice-cooling. The reaction mixture was stirred for 15 minutes under ice-cooling and 3 hours at room temperature. To the reaction mixture, ethylacetate was added and filtered. The organic layer was washed with water and concentrated in vacuo. The oily residue was purified by a silica gel column chromatography to give 0.6 g(50%) of the titled compound.

IR(film, cm$^{-1}$) 2540, 1633, 1497, 1464, 1400, 1135
Optical Rotation $[\alpha]_D^{25} - 1.8°$ (c=0.17, methanol)

Formulation Example

1) Tablet

| | |
|---|---|
| compound No.2 | 100 mg |
| crystalline cellulose | 20 mg |
| lactose | 40 mg |
| L-hydroxypropylcellulose | 5 mg |
| magnesium stearate | 5 mg |
| | 170 mg |

2) Capsule

| | |
|---|---|
| compound No.2 | 5 mg |
| magnesium stearate | 3 mg |
| lactose | 142 mg |
| | 150 mg |

By changing the ration of the compound No. 2 and lactose, capsules, which contains 10 mg, 30 mg, 50 mg, or 10 mg of the compound No. 2, were prepared.

3) Granule

| | |
|---|---|
| compound No.2 | 50 mg |
| lactose | 54 mg |
| crystalline cellulose | 20 mg |
| polyvinylpyrrolidone K-30 | 5 mg |
| magnesium stearate | 1 mg |
| | 130 mg |

PHARMACOLOGICAL TEST

The rat liver disorder model caused by CCl$_4$ is generally used to examine the efficacy of a drug for liver diseases.

We examined the efficacy of the compound(s) of this invention on liver disorder using the rat model. Furthermore, we examined the immunomodulating effect of the compound(s) of this invention using immunoresponse against sheep red blood cells of mouse, which is generally used to examine the efficacy on immune system.

1) The effect on the liver disorder caused by CCl$_4$.

The test compound was suspended in tragacanth gum solution and administered orally to male Wistar rats (5 rats a group) at a dose of 300 mg/kg.

Thirty minutes later, CCl$_4$ a liver disorder inducer, was given intraperitoneally at a dose of 0.25 ml/kg.

Serum GOT and GPT levels were measured 24 hours after the administration of CCl$_4$. To a control, 0.5% tragacanth gum solution was given. The results of the experiment with the compound No. 2, a typical compound of this invention, is shown in the Table 1.

Table 1

| Test Compound | GOT | GPT |
|---|---|---|
| Control | 18693 | 10026 |
| Compound No.2 | 13605 | 6558 |

As shown in Table 1, the activity of serum transaminase of the group given the compound of the invention was significantly lower than that of the control. The result proved that the compound of this invention has an excellent effect on liver disorder.

2) The effect on immune response against sheep red blood cells of mouse.

According to the method of Iso ( Int. J. Immunotherapy, 1, 93 (1985)), 5×10$^8$ sheep red blood cells were administered intraperitoneally to female BALB/c mice (3 to 5 mice a group) and immunized.

After immunization, the test compound suspended in 1% methyl cellulose solution was administered continuously for 4 days.

Mice were killed and the number of haemolytic plaque-forming spleen cells were measured.

50% suppressive dose was calculated based on the cell count. For a comparison, the similar test with the known compound of the formula[VI] described in U.S. Pat. No. 4305958 was performed.

The results are shown in Table 2.

Table 2

| Test Compound | 50% suppressive dose |
|---|---|
| Compound No.2 | 19.1 mg/kg |
| known compound | 90.6 mg/kg |

As shown in Table 2, the compound of this invention shows excellent immunosuppressive effect and its effect is more potent than that of the known compound.

TOXICITY TEST

Acute Toxicity

The compound No. 2 was suspended in 0.5% methyl cellulose solution at 20% concentration. The solution was administered orally to ddY mice (male, 5 weeks age, 6 mice a group) at a dose of 2000 mg/kg.

Result

Toxicity of the compound No. 2 was weak with a single case of death.

$LD_{50}$ was over 2000 mg/kg.

We claim:

1. A compound of the formula (I),

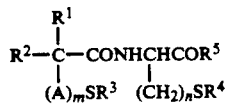

wherein $R^1$ and $R^2$ are methyl;
$R^3$ and $R^4$ are hydrogen; and
$R^5$ is hydroxy, lower alkoxy, amino or lower alkylamino;
or a pharmaceutically acceptable salt thereof.

2. N-(2,2-dimethyl-3-mercaptopropionyl)-L-cysteine as in claim 1.

3. The compound of claim 1, wherein
$R^1$ is methyl;
$R^2$ is methyl;
$R^3$ and $R^4$ are hydrogen; and
$R^5$ is hydroxy, lower alkoxy or amino.

4. The compound of claim 3, wherein $R^5$ is lower alkoxy.

5. The compound of claim 3, wherein $R^5$ is amino.

UNITED STATES PATENT AND TRADEMARK OFFICE
CERTIFICATE OF CORRECTION

PATENT NO. : 5,292,926
DATED : March 8, 1994
INVENTOR(S) : MORITA et al It is certified that error appears in the above-identified patent and that said Letters Patent is hereby corrected as shown below:

On the title page, right column, [56] References Cited, U.S. PATENT DOCUMENTS, above "Primary Examiner" insert --4,255,446   3/1981   Iwao et al

OTHER DOCUMENTS

Chemical Abstracts, Vol. 94, 104346j of Japanese 51021/1980.--

On the title page, right column, [57] "ABSTRACT", delete the entire abstract (comprising 4 lines and the formula [I]) and in its place insert --A compound of the formula

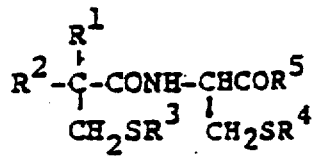

UNITED STATES PATENT AND TRADEMARK OFFICE
CERTIFICATE OF CORRECTION

PATENT NO. : 5,292,926
DATED : March 8, 1994
INVENTOR(S) : MORITA et al It is certified that error appears in the above-identified patent and that said Letters Patent is hereby corrected as shown below:

wherein $R^1$ and $R^2$ are the same lower alkyl, $R^3$ and $R^4$ are the same or different and are selected from the group consisting of hydrogen, lower alkyl, lower alkanoyl, optionally substituted phenyl lower alkyl and optionally substituted phenylcarbonyl and wherein the optional substituents are lower alkyl, lower alkoxy or halogen and $R^5$ is hydroxy, lower alkoxy, amino or lower alkylamino or a pharmaceutically acceptable salt thereof. Such compound is useful for treating liver diseases such as rheumatoid arthritis.--.

Column 11, lines 10-14, claim 1, delete all of the subject matter on these lines and insert -- 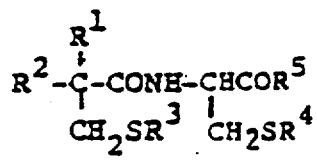 (I) --.

Signed and Sealed this

Fourteenth Day of November, 1995

Attest:

BRUCE LEHMAN

Attesting Officer

Commissioner of Patents and Trademarks